United States Patent [19]

Sato et al.

[11] Patent Number: 4,999,442
[45] Date of Patent: Mar. 12, 1991

[54] ORGANO-TITANIUM COMPOUNDS AND SURFACE TREATING AGENTS

[75] Inventors: Masayuki Sato, Tokyo; Noriyuki Kobayashi, Ichihara; Akihiko Funamoto, Abiko; Yoshitoshi Kataoka, Ichihara, all of Japan

[73] Assignee: Nippon Soda Co., Ltd., Tokyo, Japan

[21] Appl. No.: 369,812

[22] Filed: Jun. 22, 1989

Related U.S. Application Data

[63] Continuation-in-part of Ser. No. 66,360, Jun. 8, 1987.

[51] Int. Cl.$^5$ ............................................. C07F 7/28
[52] U.S. Cl. ........................................ 556/14; 556/13
[58] Field of Search .................... 556/13, 51, 54, 14

[56] References Cited

U.S. PATENT DOCUMENTS 4,080,353 3/1978 Monte et al. ................ 556/14 X
4,261,913 4/1981 Monte et al. ..................... 556/13
4,277,415 7/1981 Sugerman et al. ............. 556/14 X

*Primary Examiner*—Arthur C. Prescott
*Attorney, Agent, or Firm*—Joseph C. Mason; George Oujevolk

[57] ABSTRACT

The new organo-titanium compound offered by this invention is an alkoxy titanium acylate derivative with a coordinated phosphite diester (phosphonate diester), and a useful compound as an effective component for a surface treating agent.

The said compound is applied to the surface of a solid substance, particularly of a filler to be added to a polymer system, for modifying the surface of the filler.

The application of the said compound to a composite system consisting of an organic medium and a filler allows to reduce the viscosity of the composite system, to improve the dispersion of the filler in the composite system and to improve the mechanical properties of the cured substance of the composite system.

2 Claims, No Drawings

ORGANO-TITANIUM COMPOUNDS AND SURFACE TREATING AGENTS

This application is a continuation-in-part of U.S. patent application Ser. No. 07/066,360 filed Jun. 8, 1987.

TECHNOLOGICAL FIELD

This invention relates to a new organo-titanium compound and more particularly to an alkoxy titanium acylate derivative with a coordinated phosphite diester (phosphonate diester).

The invention also relates to a surface treating agent containing said compound as an effective component.

Generally speaking, a polymer system is used as a composite system to which a filler is added and mixed as hereinafter described.

The present invention relates to an organo-titanium surface treating agent used for improving the dispersibility of the filler in the polymer medium by modifying the surface of the filler in a solid substance, e.g. in a composite polymer system in which a polymer substance is compounded with a filler, and to improve the physical properties of the composite polymer system, as well as the organo-titanium compound which is its effective component.

BACKGROUND OF THE INVENTION

As hereinbefore stated, a polymer system is conventionally used as a composite system to whcih a filler is added and mixed so as to improve the properties such as dimensional stability and heat resistance.

However compounding a polymer system with a filler results in reducing the processability or lowering mechanical properties.

According to known methods, a substance such as a surface active agent or metal soap is added to the composite system as a means to solve these problems.

These methods however have not given fully satisfactory results as yet.

In addition to the above, the addition and use of silane compounds, i.e., a so-called a silane coupling agent, to the aforementioned composite system is known as a method to eliminate these defects. (Encyclopedia of Polymer Science and Technology, Vol. 6, p627, Interscience Publishers (1967)).

The silane coupling agent is not always effective, depending on the chemical composition, type of filler, etc., of the polymer system, i.e., the composite system (Polymer Digest, Vol. 34, Mar., p23 (1982); Plastic Age. Aug., p61 (1981).

The use of an organo-titanium coupling agent with an organo-titanium compound as an effective component, as a substitute for the silane coupling agent is proposed. (Polymer digest, Vol 34, Mar., p23 (1982); Vol. 34, May, p40 (1982)).

However the organo-titanium coupling agents known in the art, as described in the above references, have been recognized to improve the dispersibility of the filler in the composite system but are less effective to increase the strength of the cured substance of the composite system resin.

These organo-titanium compounds may be effective to decrease the viscosity of the mixed system when a filler is blended into a polymer medium but does not sufficiently improve the dispersibility of the filler into the polymer medium. On the contrary, depending on a polymer medium used, the density might be increased.

In addition to the above, the methods of using these organo-titaium coupling agents and the treatment methods of the composite systems are complicated.

PURPOSES OF INVENTION

This invention proposes to offer an organo-titanium surface treating agent which can be applied, and which is less dependant on types of fillers and polymer media used, when a filler is dispersed into a polymer medium, and also is excellent in the improvement of dispersibility and physical properties of the filler-polymer system, and to offer a new organo-titanium compound.

DISCLOSURE OF INVENTION

The repeated earnest studies of the inventors to attain the purposes mentioned above result in finding that new derivatives of alkoxy titanium acylates, which are used as effective components in conventional organo-titanium surface treating agents, to which a phosphite diester (phosphonate diester) is coordinated, are excellent in coupling between the polymer medium and the filler.

This invention relates to an organo-titanium compound represented by general formula (I) shown below:

R is a radical selected from the group consisting of alkyl radicals and alkenyl radicals, having from 1 to 8 carbon atoms, R' is a radical selected from the group consisting of alkyl radicals, alkenyl radicals and aryl radicals, substituted or not substituted, having from 1 to 22 carbon atoms, R" is a radical selected from the group consisting of alkyl radicals, alkenyl radicals and aryl radicals, substituted or not substituted, having from 3 to 22 carbon atoms, R, R' and R" may be the same or different, provided that each is selected from the group indicated n is an integer from 1 to 3, and m is 1 or 2)

and to a surface treating agent with the said organo-titanium compound as an effective component.

In this invention, the above organo-titanium compound is synthesized by reacting the following (A), (B) and (C) components.

Component (A): a tetraalkoxy titanium compound represented by general formula (II)

(where R is as defined above)

Component (B): a carboxylic acid represented by general formula (III)

(where R' is as defined above)

Component (C): a phosphite diester represented by general formula (IV) or its tautomer, phosphonate diester

(where R" is as defined above).

In the invention, the —(OR) groups in the above general formulae, (I) and (II), are hydrolytic groups whose R radicals are the same or different radicals selected from the group consisting of alkyl radicals and alkenyl radicals having from 1 to 8 carbon atoms.

In the organo-titanium compounds represented by general formula (I) mentioned above, a compound having long-chain substitutes in which R has reduced affinity with the filler when used as an effective component of a surface treating agent.

In the synthesis of the organo-titanium compound represented by general formula (I), Component (A), if a tetraalkoxy titanium compound having long-chain substitutes in which R has more than 8 carbon atoms, is less reactive with Components (B) and (C).

A typical compound of Component (A) represented by general formula (II) mentioned above and used for the synthesis of the organo-titanium compound represented by above general formula (I) includes $Ti(OC_3H_7)_4$, $Ti(OC_4H_9)_4$, $Ti(OC_8H_{17})_4$, $Ti(OCH_2CH=CH_2)_4$ or $Ti(C_4H_9O)(C_3H_7O)_3$.

The —(OCOR') group in general formula (I) mentioned above and the R'COO— group in general formula (III) are lipophilic carboxylate residual groups with affinity with the polymer medium, in which R' is an alkyl radical, an alkenyl radical or an aryl radical, substituted or not substituted, having from 1 to 22 carbon atoms.

Examples of a substitute for R' include a halogen atom, a hydroxyl group, an amino group, a nitro group, a mercapto group and an epoxy group.

In the organo-titanium compound represented by general formula (I), R's may be different radicals.

In the synthesis of the organo-titanium compound represented by general formula (I), Component (B) is hard to handle for the synthetic reaction if R' in general formula (III) is a carboxylic acid with a long-chain substitute having more than 22 carbon atoms because the component is solid at room temperature.

A typical compound of Component (B) represented by general formula (III) and used for the synthesis of the organo-titanium compound represented by general formula (I) includes $CH_3COOH$, $C_2H_5COOH$, $C_3H_7COOH$, $C_4H_9COOH$, $C_5H_{11}COOH$, $C_{12}H_{25}COOH$, $C_{17}H_{35}COOH$, $CH_2=CHCOOH$, $CH_2=C(CH_3)COOH$, $CH_2=CHCH_2COOH$, $C_8H_{17}CH=CHC_7H_{14}COOH$, $C_6H_5COOH$, $CH_3C_6H_4COOH$, $C_6H_{13}CH(OH)CH_2CH=CHC_7H_{14}COOH$, $NH_2CH_2COOH$, $NH_2C_8H_{16}COOH$, $ClCH_2COOH$, $NH_2C_6H_4COOH$, $ClC_6H_4COOH$, $HOC_6H_4COOH$, $HSCH_2COOH$ or

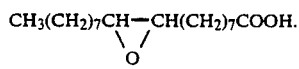

In the invention, the coordinated group, $(H(O)P(OR'')_2)$, in general formula (I) mentioned above and the $H(O)P(OR'')_2$ compound represented by general formula (IV) are phosphite diester or phosphonate diester of its tautomer in which R"s are the same or different radicals selected from the group consisting of alkyl radicals, alkenyl radicals and aryl radicals, substituted or not substituted, having from 3 to 22 carbon atoms.

Examples of a substitute for R" include halogen atoms and alkyl radicals.

The use of the organo-titanium compound represented by general formula (I) in which R" has less than 3 or more than 22 carbon atoms, as an effective component of the surface treating agent, gives no recognized expected coupling effect between the polymer medium and the filler in either case.

A typical compound of component (C)-represented by general formula (IV) and used for the synthesis of the organo-titanium compound represented by general formula (I) includes $(C_4H_9O)_2P(O)H$, $(C_8H_{17}O)_2P(O)H$, $(C_{12}H_{25}O)_2P(O)H$, $((C_4H_9O)(C_8H_{17}O))P(O)H$, $(C_6H_5O)_2P(O)H$, $(HOC_6H_4C_3H_{17}O)_2P(O)H$, $(CH_2=CHCH_2O)_2P(O)H$, $(ClCH_2CHClCH_2O)_2P(O)H$, $(CH_2=C(CH_3)COOC_2H_4O)_2P(O)H$, or $(CH_3CH_2OCH_2CH_2O)_2P(O)H$.

The organo-titanium compound of the invention, as represented by general formula (I) shown above, has a phosphite diester (phosphonate diester) coordinated to the alkoxy titanium acylate and thanks to its polarity the dissolution of the organo-titanium compound into an organic medium is increased.

Therefore, the affinity with a variety of polymer media increases while keeping the hydrolytic and lipophilic properties the alkoxy titanium acylate has.

In the synthesis of the organo-titanium compound represented general formula (I), the presence of phosphite diester (phosphonate diester) prevents the organo-titanium compound from crystallizing which may occur if Component (B) is a carboxylic acid with a functional group.

The organo-titanium compound of the invention has a hycrolytic-(OR) group with large affinity with a filler, a —(OCOR') group with large affinity with an organic medium and a —$(H(O)P(OR'')_2)$ group, thereby being suitable as an effective component of organo-titanium surface treating agent.

The organo-titanium compound of the invention can be synthesized by any one of the following synthetic methods.

(a) A method wherein the aforementioned 3 components, (A), (B) and (C), are simultaneously reacted.

(b) A method wherein Components (A) and (B) mentioned above are first reacted then Component (C) is reacted.

(c) A method wherein Components (A) and (C) mentioned above are first reacted and then Component (B) is reacted.

If Component (B) is carboxylic acid having an additional group, method (a) or (c), more preferably method (c), is employed.

The reaction, depending on a type of Component (B) used, is usually carried out by stirring for 0.5 to 48 hours at reaction temperature between room temperature and 150° C.

When the reaction product is used as a surface treating agent, a reaction ratio of Components (A), (B) and (C) is, to 1 mole of Component (A), 0.5–3.0 moles of Component (B) and 0.5–3.0 moles of component (C) more preperably, to 1 mole of Component (A), 1.0–2.0 moles of Component (B) and 1.0–2.0 moles of component (C).

In the above reaction ratio of the components, if Components (B) is less than 0.5 moles to 1 mole of Component (A), the production rate of the compound represented by general formula (I) in the reaction product is low and the reaction product has little desired effect when used as a surface treating agent, and if it exceeds 3.0 moles, the effect of the reaction product as a surface treating agent does not increase as expected because free fatty acids, and esters, etc. may give an adverse effect.

If Component (C) is less than 0.5 moles to 1 mole of Component (A), the desired effect is small, and if more than 3.0 moles, the effect is rather reduced.

When the reaction product is used as a surface treating agent one compound represented by general formula (I) can be singly used or a mixture of two or more compounds can be also employed The reaction product synthesized by using a mixture of two or more compounds for each component (A), (B) or (C) mentioned above as a starting material can be employed as a surface treating agent.

The organo-titanium surface treating agent of the invention is used by blending into a wide variety of a composite system of an organic medium and a filler in order to e.g. reduce the viscosity of the mixture system, improve the dispersibility of the filler into the organic medium or improve the physical properties of the composite system.

An organic medium includes mainly a polymer medium such as linseed oil, tung oil, soy bean oil, dehydrated castor oil, maleinized oil, rosin, rosin esters, acrylic resin, phenol resin, xylene resin, alkyd resin, amino resin, epoxy resin, urea resin, polyurethane resin, chlorinated rubber, cyclized rubber, nitrocellulose, polyether polyol, polyester polyol, polyethylene resin or polypropylene resin.

A plasticizer includes dioctyl phthalate or dioctyl adipate, which is blended into the polymer medium beforehand.

A filler includes a large number of fillers for blending into the above organic medium to make a composite system.

These fillers include "relatively inactive solid substances added to polymer materials in order to e.g. reduce the unit price of polymer material, improve the processability and physical properties or give color effects" (Physical Properties of filled Polymers, p8-p9, Kozo Sato, Riko Publishing Co. (1978)) and "pigments and extenders named in the coating material industry" (p9 in the same book).

A filler includes calcium carbonate, kaolin, clay mica, talc, wollastonit, calcium silicate, titanium oxide, iron oxide, silica, carbon black, calcium sulfate, barium sulfate, aluminum powder, zinc powder, glass fiber, wood powder, paper/fiber powder, and synthetic and natural fibers.

Any one of the following methods is applied as a method of using the surface treating agent of the invention but the method of using is not limited to these.
(a) A method that the surface treating agent is added to the organic medium beforehand.
(b) A method that the surface treating agent is simultaneously added when the organic medium and the filler are mixed.
(c) A method that the surface treating agent is coated on the surface of the filler beforehand.

The surface treating agent of the invention can be used concurrently with other kinds of surface treating agents within the range that the purpose is not failed.

An amount of the surface treating agent used as the organic titanium compound represented by general formula (I) mentioned above is 0.1 to 5 parts by weight, preferably 0.5 to 2 parts by weight, to 100 parts by weight of the filler.

The surface treating agent has little effect if less that 0.1 parts by weight of the agent to 100 by weight of the filler is added, and gives an increased effect, but not as much as expected if more than 5 parts by weight is added.

BEST WAYS TO CARRY OUT THE INVENTION

The best ways to carry out this invention are concretely discribed by referring to actual examples and test examples.

However the range of the invention is not limited by the following examples.

The "parts" used in the following examples stands for parts by weight unless otherwise noted.

EXAMPLE 1

Synthesis of Organo-titanium Compound

Into a 1 lit. fourneck flask equipped with a stirrer, a thermometer and a cooler was added 284 g (1 mole) of tetra-isopropoxy titanium, and 86 g (1 mole) of methacrylic acid was gradually added over an hour with stirring with care for the temperature not to exceed 35° C.

Into the generated light yellowish brown transparent solution was gradually added 388 g (2 moles) of dibutyl hydrogen phosphite over an hour in a similar manner to the above with care for the temperature not to exceed 40° C.

After the completion of the addition of dibutyl hydrogen phosphite, the stirring of the resulting solution was kept for another hour.

While keeping the obtained reaction product at 40° C., the pressure was reduced to 10 torr, for distilling 59 g of volatile matter, and Compound (T-1) was obtained as a distillation residue.

The distillate obtained was isopropanol

The reaction product of the distillation residue was assumed to be the following compound (T-1) from the molecular weight measured by vapor pressure osmometer and the values of elementary analysis.

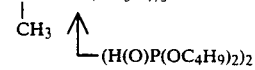

(T-1)

|  | (Found) | (Calculated) |
| --- | --- | --- |
| C | 50.1% | 49.9% |
| H | 9.4% | 9.2% |
| P | 9.1% | 8.9% |
| TiO$_2$ | 11.2% | 11.4% |
| molecular weight | 662 | 698 |

(2) Compound (T-2) and Comparison Compound (CT-1)

Into a 2 lit. 4 neck flask equipped with a stirrer, a thermometer and a cooler was added 340 g (1 mole) of tetra-n-butoxy titaium and 284 g (1 mole) of isostearic acid was dropped over an hour with stirring with care for the temperature not to raise higher than 40° C.

After the completion of the dropping of isostearic acid, while keeping the resulting solution at 40° C., the pressure was reduced to 10 torr, and 73 g of n-butanol was recovered.

The distillation residue obtained was a light yellow transparent solution, which was a comparison compound (Ct-1).

The analytical results showed that the comparison compound (Ct-1) was tri-n-butoxy titanium monoisostearate.

Then 227 g of comparison compound (CT-1) was added into a 4 neck flask arranged in a similar manner to the above, and 210 g (0.5 moles) of dilauryl hydrogen phosphite was dropped over an hour with stirring with care for the temperature not to exceed 40° C. The solution was successively stirred for another 2 hours after the dropping was completed.

The reaction solution was pressure reduced to 7 torr at 40° C., giving almost no recognizable distillates.

The reaction product was a light yellow transparent solution.

The obtained reaction product was assumed to be the following compound (T-2) from the molecular weight and the values of elementary analysis.

$$C_{17}H_{35}COOTi(OC_4H_9)_3 \quad (T\text{-}2)$$
$$\uparrow$$
$$(H(O)P(OC_{12}H_{25})_2)$$

|   | (Found) | (Calculated) |
|---|---|---|
| C | 67.5% | 66.9% |
| H | 12.2% | 11.8% |
| P | 3.0% | 3.2% |
| $TiO_2$ | 8.0% | 8.2% |
| molecular weight | 925 | 968 |

(3) Compound (T-3) and Comparison Compound (CT-2)

Into a 2 lit. 4 neck flask equipped with a stirrer, a thermometer and a cooler was added 568 g (2 moles) of tetra isopropoxy titanium, and 388 g (2 moles) of dibutyl hydrogen phosphite was gradually added over an hour with stirring with care for the temperature not to exceed 45° C.

After the completion of the addition of dibutyl hydrogen phosphite, the stirring was kept for about another hour to give an almost colorless transparent solution.

The reaction solution obtained was pressure reduced to 5 torr at 45° C., giving almost no recognizable distillates.

The reaction product obtained was comparison compound (CT-2).

478 g of comparison compound (CT-2) was placed in a 2 lit. 4 meck flask arranged in a similar manner to the above, and, while keeping the temperature at 45° C., 144 g (1 mole) of 2-ethyl hexanoic acid was gradually added over 30 minutes with stirring.

After the completion of the addition of 2-ethyl hexanoic acid, the solution was successively stirred for another hour, and then pressure reduced to 20 torr at 45° C. 59 g of isopropanol was revovered as a distillate and a reaction product was obtained as a distillation residue.

The reaction product obtained was assumed to be the following compound (T-3) from the molecular weight and the values of elementary anolysis.

$$C_7H_{15}COOTi(OC_3H_7)_3 \quad (T\text{-}3)$$
$$\uparrow$$
$$(H(O)P(OC_4H_9)_2)$$

|   | (Found) | (Calculated) |
|---|---|---|
| C | 54.0% | 53.3% |
| H | 10.0% | 9.9% |

$$C_7H_{15}COOTi(OC_3H_7)_3 \quad (T\text{-}3)$$
$$\uparrow$$
$$(H(O)P(OC_4H_9)_2)$$

|   | (Found) | (Calculated) |
|---|---|---|
| P | 5.3% | 5.5% |
| $TiO_2$ | 14.0% | 14.2% |
| molecular weight | 525 | 562 |

(4) Compound (T-4)

Into a 2 lit. 4 neck flask equipped with a stirrer, a thermometer and a cooler was added 340 g (1 mole) of tetra-n-butoxy titanium and, under the control of the temperature to 35° C. or below by cooling the outside with water, 388 g (2 moles) of dibutyl hydrogen phosphite was gradually added over 20 minutes and the redulting solution was successively stirred for another 45 minutes after the addition was completed.

Then 296 g of ricinoleic acid (neutratization value; 179, iodine number: 89, hydroxyl value: 168, Ito Oil Mfg. Co., Ltd.) was gradually added over an hour with stirring. The resulting solution was kept stirring for another hour after the addition was completed.

The reaction solution obtained was pressure reduced to 10 torr at 60° C., 72 g (0.97 moles) of n-butanol was distilled to recover, and a viscous brown transparent liquid was obtained.

The reaction product obtained was assumed to be the following compound (T-4) from the values of elementary analysis.

$$(C_4H_9O)_3TiOCOC_{17}H_{32}OH \quad (T\text{-}4)$$
$$\uparrow$$
$$(H(O)P(OC_4H_9)_2)_2$$

|   | (Found) | (Calculated) |
|---|---|---|
| C | 58.2% | 58.0% |
| H | 18.1% | 17.8% |
| P | 6.6% | 6.5% |
| $TiO_2$ | 8.3% | 8.4% |

(5) Compound (T-5) and Comparison Compound (CT-3)

Into a 1 lit. 4 neck flask equipped with a stirrer, a termometer and a cooler was added 340 g (1 mole) of tetra-n-butoxy titanium, and [94 g (1 mole) of dibutyl hydrogen phosphite was gradually added over an hour with stirring with care for the temperature not to exceed 50° C. The resulting solution was successively stirred for another about an hour after the addition was completed.

A part of the obtained reaction solution was pressure reduced to 20 torr at 50° C., giving no recognizable distillates.

Into a 4 neck flask arranged in a similar manner to the above was added 262 g of the obtained reaction solution and, while keeping the temperature to 40° C., 68.5 g (0.5 moles) of p-amino benzoid acid was added with stirring in a way that about 2 g was added one by one when the previously added crystal was dissolved completely.

It took approximately 2 hours to add p-amino benzoic acid, then the resulting solution was kept stirring for another 2 hours and a brown transparent solution was obtained.

The reaction solution obtained was pressure reduced to 10 torr at 50° C., 36 g of n-butanol was recovered, and a reaction product was obtained.

The reaction product obtained was assumed to be the following compound (T-5) from the molecular weight and the values of elementary analysis.

$$(C_4H_9O)_3TiOCOC_6H_4NH_2 \quad \text{(T-5)}$$
$$\uparrow$$
$$(H(O)P(OC_4H_9)_2)$$

|       | (Found) | (Calculated) |
|-------|---------|--------------|
| C     | 55.0%   | 54.3%        |
| H     | 9.0%    | 8.8%         |
| N     | 2.4%    | 2.3%         |
| P     | 5.3%    | 5.2%         |
| TiO$_2$ | 13.0%  | 13.4%        |
| molecular weight | 553 | 597 |

The reactions and treatments were repeated in the same conditions as those for the synthesis of Compound (T-5) except that 20 g of p-amino benzoic acid was added, and comparison compound (CT-3) was obtained. The compound obtained (T-5) and comparison compound (CT-3) were soluble in epoxy resin (Epicoat 828) of an amount of 20 times and in polyether (Diol-1000, Mitsui Nisso Urethane Co., Ltd.).

The reactions and treatments were again repeated completely in the same conditions as those for the synthesis of compound (T-5) except that dibutyl hydrogen phosphite was not used, and a highly viscous orange-red solution was obtained.

The reaction product obtained gave distilled n-butanol of almost equal amount to that of this reaction eoamples. However, the product was an extremely highly viscous gummy substance and was not dissolved completely in the above epoxy resin and polyether.

(6) Compound (T-6) and Comparison Compound (CT-4)

Into a 2 lit. 4 nick flask equipped with a stirrer, a thermometer and a cooler was added 340 g (1 mole) of tetra-n-butoxy titanium and, under the control of the temperature to 40° C. or below by cooling the outside with water, 836 g (2 moles) of dilauryl hydrogen phosphite was gradually added over an hour with stirring. The resulting solution was kept stirring for another 30 minutes after the addition was completed.

While keeping the stirring and maintaining the temperature to 40° C., 92 g (1 moles) of thioglycolic acid was gradually added over an hour and the resulting solution was successively stirred for another hour after the addition was completed.

The resulting solution was left standing for a day and a night, and then heated to 60° C. under reduced pressure of 10 torr for removing the side product of n-butanol by distillation, giving a reaction product.

The amount of n-butanol by distillation, giving a reaction product.

The reaction product obtained of orange yellow transparent liquid was assumed to be the following compound (T-6) from the values of elementary analysis.

$$(C_4H_9O)_3Ti\text{—}OCOCH_2SH \quad \text{(T-6)}$$
$$\uparrow$$
$$(H(O)P(OC_{12}H_{25})_2)_2$$

|       | (Found) | (Calculated) |
|-------|---------|--------------|
| C     | 63.0%   | 62.3%        |
| H     | 11.5%   | 11.1%        |
| S     | 2.7%    | 2.7%         |
| P     | 5.3%    | 5.2%         |
| TiO$_2$ | 6.9%   | 6.7%         |

A procedure was repeated completely in the same conditions as those for the synthesis of compound (T-6) except that thioglycolic acid was not added and comparison compound (CT-4) was obtained.

The pressure reduction of comparison compound (CT-4) gave no n-butanol distilled.

The direct addition of thioglycolic acid to tetra-n-butoxy titanium without adding dilauryl hydrogen phosphite resulted in forming yellow crystal.

The crystal obtained was not dissolved in toluene of 10 times the amount, nor in isopropanol, polyethers and epoxy resin (Epicoat-828).

EXAMPLE 2

Use as a Surface Treating Agent (1) Reduction in viscosity of organic medium-filler composite system (a) Eposyresin-titanium oxide system A hundred parts of epoxy resin (Epicoat-828, Yuka Shell Epoxy Kabushikikaisha), 0.5 parts of each of the organo-titanium compounds synthesized in Example 1 and 50 parts of titanium oxide (Ishihara Sangyo Kaisha, Ltd.) were well kneaded in a ball mill and the kneaded product was measured for the viscosity at 25° C.

For comparison, commercially available surface treating agents were used in the same conditions and the obtained kneaded products were measured for the viscosity at 25° C.

(Commercially available surface treating agents used)

KR-TTS: Ti (OC$_3$H$_7$)(OCOC$_{17}$H$_{33}$)$_3$: (Kenrich Petrochemicals, Inc.)

KR-41B: Ti (OC$_3$H$_7$)$_4$ (P(OC$_8$H$_{17}$)$_2$OH)$_2$: (Kenrich Petrochemicals, Inc.)

The measured results of viscosity are shown in Table 1.

(b) Epoxy resin-calcium carbonate system

A hundred parts of epoxy resin (Epicoat-828, as described above), 1.0 part of each of the organo-titanium compounds synthesized in Example 7 and 100 parts of calcium carbonate (Shiraishi Kogyo Kaisha, Ltd.) were well kneaded in a ball mill and the kneaded was measured for the viscosity at 25° C.

For comparison the commercially available surface treating agents (as described above) and dibutyl hydrogen phosphite (DBHP), a raw material for the synthesis of the organo-titanium compounds, were used in the same conditions and the obtained kneaded products were measured for the viscosity at 25° C.

The measured results of viscosity are shown in Table 1.

TABLE 1

| Organic titanium compound (Surface treating agent) | Viscosity CPS (25° C.) | |
|---|---|---|
| | (a) TiO$_2$ System | (b) CaCO$_3$ System |
| Example | | |
| T-1 | 22,000 | 56,000 |
| T-2 | 23,000 | 65,000 |
| T-3 | 23,000 | 57,000 |
| T-4 | 24,000 | — |
| T-5 | 26,000 | — |
| T-6 | 30,000 | — |
| Comparison example | | |
| — | 63,000 | 86,000 |
| CT-1 | 66,000 | 100,000< |
| CT-2 | 24,000 | — |
| CT-3 | 25,000 | — |
| CT-4 | 35,000 | — |
| KR-TTS | 64,000 | 100,000< |
| KR-41B | 41,000 | 77,000 |
| DBHP | — | 87,000 |

As shown in Table 1, the organo-titanium compounds of the invention, which are chelated with an organic phosphonate, have an excellent effect of viscosity reduction in the organic medium-filler systems.

(2) Dispersion of filler in organic medium-filler composite system (a) Epoxy resin-titanium oxide system A hundred parts of Epicoat-828 (as described above), 0.5 parts of each of organo-titanium compounds synthesized in Example 1, 50 parts of titanium oxide (as described above) and 37 parts of xylene were well mixed for a fixed time by using a paint shaker. The resulting mixture was measured for the viscosity at 25° C.

The obtained mixture was placed in a test bottle of 8 cm in inner diameter and 15 cm high so that the solution was 10 cm high in the bottle. The bottle was covered with a lid and left standing at room temperature for a week in order to study the dispersion stability of the filler according to the presence or absence of precipitate.

For comparison the aforementioned commercially available surface treating agents, and dibutyl hydrogen phosphite (DBHP) and dilauryl hydrogen phosphite (DLHP) which were used as a material for the synthesis of the organo-titanium compounds of the invention were used and treated in a similar manner to the above for the study of viscosity and dispersibility.

The results are shown in Table 2.

(b) Polyether polyol-calcium carbonate system

A hundred parts of polyether polyol (Diol-3000, Mitsui Nisso Urethane Co., Ltd.), 30 parts of dioctyl phthalate, 0.6 parts of each of the organotitanium compounds synthesized in Example 1 and 60 parts of calcium carbonate (as described above) were kneaded and the kneaded was measured for the viscosity at 25° C.

The presence or absence of precipitated calcium carbonate in the obtained kneaded product a month after the kneading, was studied in a similar manner to the above. The dispersion stability was checked by a degree of difficulty to re-disperse the precipitate.

For comparison the aforementioned commercially available surface treating agents and dibutyl hydrogen phosphite (DBHP) used as a material for the synthesis of the organo-titanium compounds of the invention were used and a similar treatment procedure was repeated to check the viscosity and dispersibility.

The results are shown in Table 2. In Table 2, ⊙ stands for no precipitation and extremely easy re-dispersion, and ○ stands for with precipitation but easy re-dispersion.

TABLE 2

| Organic titanium compound (Surface treating agent) | (a) Epoxy system | | (b) Polyether system | |
|---|---|---|---|---|
| | Viscosity CPS | Dispersion stability | Viscosity CPS | Dispersion stability |
| Example | | | | |
| T-1 | 160 | no precipitate | 680 | ⊙ |
| T-2 | 350 | no precipitate | 700 | ⊙ |
| T-3 | 265 | no precipitate | 660 | ⊙ |
| T-4 | — | — | 780 | ⊙ |
| T-5 | — | — | 820 | ⊙ |
| T-6 | — | — | 810 | ⊙ |
| Comparison example | | | | |
| — | 770 | precipitate | 7,100 | ⊙ |
| CT-1 | 490 | precipitate | 8,200 | ⊙ |
| CT-2 | — | — | 650 | ○ |
| CT-3 | — | — | 810 | ○ |
| CT-4 | — | — | 920 | ○ |
| KR-TTS | 480 | precipitate | 8,200 | ⊙ |
| KR-41B | 380 | precipitate | 700 | ○ |
| DBHP | 610 | precipitate | 2,300 | ⊙ |
| DLHP | 560 | precipitate | — | — |

In the table DBHP means dibutyl hydrogen phosphite and DLHP is dilauryl hydrogen phosphite.

As shown in Table 2, the organo-titanium compounds of the invention have an excellent effect of a reduction in viscosity in the organic mediumfiller composite systems as well as excellent dispersion stability of the filler in the mixture system.

(3) Resin-filler composite cured substance (a) Urethane cured substance

Sixty parts of calcium carbonate (as described above) was coated with 1.0 part of each of the organo-titanium compounds synthesized in Example 1 by using a Henschell mixer.

To the obtained coated product were added 100 parts of polyether polyol (MN-3050K, Mitsui Nisso Urethane Co., Ltd.), and 10.5 parts of polyether polyol (MNT-300, Mitsui Nisso Urethane Co., Ltd.), and the mixture was well kneaded. The kneaded mixture was measured for the viscosity at 25° C.

To the kneaded product obtained was added an isocyanate compound (MDILK, Mitsui Nisso Urethane Co., Ltd.) at a ratio of NCO/OH=1.05 and they were mixed at room temperature. The resulting mixture was poured in a mold and heated at 120° C. for 4 hours for curing.

The cured product obtained was heat treated at 100° C. for 4 days. The hardness, tensile strength and elongation at break of the product before and after the heat treatment were measured.

For comparison various tests were carried out in a similar method to the above by employing a system with no surface treating agent blended, and blending systems using the aforementioned commercially available surface treating agents and dibutyl hydrogen phosphite (DBHP) and dilauryl hydrogen phosphite (DLHP) which were used as a material for the synthesis of the organo-titanium compounds of the invention.

The results are shown in Table 3.

TABLE 3

| Organic titanium compound (Surface treating agent) | Kneaded viscosity CPS | Hardness shore A | Tensile strength Kg/cm² | Elongation at break % |
|---|---|---|---|---|
| Example | | | | |
| T-1 | 1300 | 79/77 | 38.3/38.6 | 92.5/95.5 |
| T-2 | 1200 | 81/80 | 38.0/38.6 | 91.8/93.0 |
| T-3 | 1200 | 80/79 | 39.0/39.5 | 92.1/93.0 |
| T-4 | 1400 | 85/84 | 46.0/46.0 | 88.6/89.0 |
| T-5 | 1600 | 88/87 | 47.5/47.0 | 87.0/86.2 |
| T-6 | 1300 | 87/86 | 46.5/46.7 | 88.0/88.0 |
| Comparison example | | | | |
| — | 2800 | 78/73 | 36.8/34.2 | 86.5/96.7 |
| CT-1 | 3000 | 76/75 | 35.7/34.2 | 72.5/70.0 |
| CT-2 | 1300 | 72/64 | 35.8/33.2 | 91.0/90.0 |
| CT-3 | 1300 | 79/78 | 37.8/37.8 | 89.5/89.0 |
| CT-4 | 1400 | 74/70 | 36.8/33.8 | 91.0/90.0 |
| KR-TTS | 3100 | 76/74 | 35.8/35.0 | 73.0/70.0 |
| KR-41B | 1200 | 73/65 | 36.1/32.5 | 91.0/91.5 |
| DBHP | 2600 | 71/63 | 34.1/31.0 | 91.0/81.0 |
| DLHP | 2500 | 72/60 | 34.5/31.0 | 92.0/93.5 |

In the table, the numerator stands for the value before the heat treatment and the denominator is the value after the heat treatment.

(b) Polypropylene cured substance

A hundred parts of calcium carbonate (as discribed above) was coated with 1.5 parts of each of the organo-titanium compounds synthesized in Example 1 by using a Henschell mixer.

Then the coated product obtained was added to 100 parts of polypropylene resin (Ube Industries, Ltd.). The mixture was kneaded by a two-rod roll heated to 165°–170° C. for 15 minutes and pulverized.

The melt viscosity of the pulverized products obtained was measured by melt indexer (JIS-k-6760).

These pulverized products were molded by thermal pressing (200° C.×500 kg/cm²) for 7 minutes for the measurements of such properties as Izod impact value (JIS-k-6740), tensile strength and elongation at break.

The results are shown in Table 4.

TABLE 4

| Organic titanium compound (Surface treating agent) | Melt index g/10 min. | Izot impact value Kg/cm² | Tensile strength Kg/cm² | Elongation at break % |
|---|---|---|---|---|
| Example | | | | |
| T-1 | 5.3 | 4.7 | 265 | 41 |
| T-2 | 6.0 | 5.9 | 251 | 56 |
| T-3 | 5.8 | 5.6 | 258 | 49 |
| Comparison example | | | | |
| — | 2.5 | 3.6 | 255 | 31 |
| CT-3 | 5.0 | 4.1 | 240 | 39 |
| KR-TTS | 5.0 | 4.0 | 240 | 42 |
| PP | 6.5 | 7.0 | 295 | approx. 600 |

In the table, PP stands for pure polypropylene.

(C) Epoxy cured sub tances

By using a Henschell mixer, 1 kg of calcium carbonate (Whiton SSB, Shiraishi Kogyo Kaisha, Ltd.) was added to a 2% concentration isopropanol solution containing 10 g of each of the organo-titanium compounds synthesized in Example 1 and the resulting solution was stirred for 2 hours at room temperature and then dried under reduced pressure, giving coated powder.

A hundred grams of the coated powder obtained and 200 g of epoxy resin (Epicoat-828, as described above) were kneaded by a ball mill.

Fifty grams of the kneaded product obtained was mixed with 35 g of a mixture of 100 g of pyromellitic acid and 400 g of methyl nadic anhydride. After molding and defoaming, the resulting mixture was heated at 100° C. for 2 hours and for another 2 hours at 180° C., giving a molding.

The bending strength of the obtained moldings is shown in Table 5.

TABEL 5

| Organic titanium compound (Surface treating comp.) | Bending strength Kg/mm² |
|---|---|
| Example | |
| T-3 | 15.6 |
| T-5 | 17.2 |
| T-6 | 16.8 |
| Comparison example | |
| — | 14.2 |
| CT-3 | 14.8 |
| CT-4 | 12.8 |
| KR-TTS | 10.2 |
| KR-41B | 9.8 |
| DLHP | 11.0 |

(4) Organic medium-filler composite coat film
Acrylic-titanium oxide system

A hundred parts of acrylic resin (Acrydic A-166, Dai Nippon Ink Co.), 2.4 parts of each of the organo-titanium compounds synthesized in Example 1, 240 parts of titanium oxide (as described above) and 200 parts of xylene were well mixed to give a mixture.

The mixture obtained was measured for the viscosity at 25° C. and tested for the ability to remain level and as a coating film.

For comparison, the aforementioned commercially available surface treating agents were used.

The results are shown in Table 6.

The leveling ability in Table 6 is represented by 3 grades, A, B and C, in the order from the better.

The gloss of coat film is represented by 60° specular reflection factor measured by using a glossimeter of Type GM-3.

TABLE 6

| Organic titanium compound | Viscosity CPS | Leveling ability. | Gloss % | Pencil Hardness |
|---|---|---|---|---|
| Example | | | | |
| T-1 | 2700 | A | 18.0 | HB |
| T-2 | 2500 | A | 17.0 | HB |
| T-3 | 2400 | A | 18.5 | H |
| Comparison example | | | | |
| — | 40000 | C | 12.5 | HB |
| CT-2 | 4900 | B | 17.5 | HB |
| KR-TTS | 2900 | B | 13.0 | HB |
| KR-41B | 5800 | B | 14.0 | HB |

(5) Coating of steel plate

Each of the organo-titanium compounds synthesized in Example 1 was diluted 8 times with n-hexane. The diluted solution was sprayed to make a coat on a chromated steel plate so that the dry film is approximately 1 $\mu$ thick. The plate was dried at 80° C. for 30 minutes, giving a coated steel plate.

A finger print staining test and rust prevention tests of 48 hours and 168 hours by salt spray were performed for the obtained coated steel plate.

The test results are shown in Table 7.

TABLE 7

| Organic titanium compound | Finger print staining | Rust generation 48 hours | 168 hours |
|---|---|---|---|
| Example | | | |
| T-1 | No | No | No |
| T-2 | No | No | No |
| T-3 | No | No | No |
| Comparison | | | |
| — | Yes | Yes | Yes |
| KR-TTS | Yes | No | No |
| DBHP | No | No | Yes |

As shown in Table 7, the organo-titanium compounds of the invention allow to make a coat, which is not stained by finger prints as well a has excellent rust preventive ability, on a steel plate.

INDUSTRIAL APPLICABILITY

A surface treating agent containing the organic titanium compound of the invention as an effective component gives various numerous effects, as shown in the examples described above, particularly by using it to blend into a composite system of a polymer medium and a filler. When a filler is dispersed into a polymer medium in particular, the said agent has extremely excellent effects for reducing the viscosity of the mixture system, improving the dispersibility of the filler and improving the physical properties of the composite system.

Concretely obtained effects are listed below.
(a) For coating materials and printing ink
  (i) Improvement of gloss or hiding power
  (ii) Improvement of leveling ability
  (iii) Reduction in viscosity of composite system
  (iv) Saving of solvents (diluting agents)
  (v) Increase in a filling ratio of filler
  (vi) Reduction in mixing time when manufacturing
(b) For polymer compounds for molding processing
  (i) Improvement of flowability
  (ii) Increase in a filling ratio of filler
  (iii) Improvement of physical properties
  (iv) Reduction in mixing dispersing time The organo-titanium surface treating agents of the invention with the above properties are thus applicable to a variety of mixture systems of various kinds of organic media and fillers such as composite systems of matter with organic polymer media, in order to improve such cases as the dispersion of a pigment into a coating material, printing ink, etc., the dispersion of a filler into a resin material to be molded by casting or molding processing, the affinity between the fiber and the resin of the matrix in a fiber composite material or the adhesiveness between the surface of metal and a coating material.

The said surface treating agent is available as a surface treating agent for steel plates. As shown in the above example, the coating of the surface treating agent on a steel plate improves the properties of the plate such as resistance against finger print staining and rust prevention.

This invention offers a surface treating agent applicable to wide fields of the industries and a new organo-titanium compound as an effective component of the agent, thereby having an extremely great industrial significance.

We claim:

1. An organic titanium compound represented by the following following formula (I)

$$(RO)_n-Ti-(OCOR')_{4-n} \quad (I)$$
$$\quad \uparrow$$
$$\quad (H(O)P(OR'')_2)_m$$

wherein Rs are the same or different radicals selected from the group consisting of alkyl radicals and alkenyl radicals, having from 1 to 8 carbon atoms,
R's are the same or different radicals selected from the group consisting of alkyl radicals and alkenyl radicals and aryl radicals, substituted or not substituted, having from 1 to 22 carbon atons,
R"s are the same or different radicals selected from the group consisting of alkyl radicals, alkenyl radicals and aryl radicals, substituted or not substituted, having from 3 to 22 carbon atoms,
n is an integer from 1 to 3, and
m is 1 to 2.

2. A method for the preparation of the organo-titanium compound of claim 1 represented by the following formula (I), which comprises reacting components (A), (B) and (C) described below:

$$(RO)_n-Ti-(OCOR')_{4-n} \quad (I)$$
$$\quad \uparrow$$
$$\quad (H(O)P(OR')_2)_m$$

wherein R, R', R", n and m are as defined above:
component (A): a tetra-alkoxy titanium compound represented by formula (II) shown below $$Ti(OR)_4 \quad (II)$$

wherein R is as defined above,
component (B): a carboxylic acid represented by formula (III) shown below $$R'COOH \quad (III)$$

wherein R' is as defined above,
component (C): a phosphite diester or a phosphonate diester represented by formula (IV) shown below $$(R''O)_2P(O)H \quad (IV)$$

wherein R" is as defined above.

* * * * *